United States Patent [19]

Rosenberg

[11] 4,175,553

[45] Nov. 27, 1979

[54] LUMBOSACRAL-ORTHOSIS ORTHOPEDIC SUPPORT

[75] Inventor: Henry W. Rosenberg, East Brunswick, N.J.

[73] Assignee: Camp International, Inc., Jackson, Mich.

[21] Appl. No.: 859,088

[22] Filed: Dec. 9, 1977

[51] Int. Cl.² ............................................. A61F 5/02
[52] U.S. Cl. ............................................ 128/78; 2/44
[58] Field of Search ...................... 128/78, 95–96, 128/518 R, 520, 538, 549, 567, 570, 573, 578; 2/44

[56] References Cited

U.S. PATENT DOCUMENTS

| 3,351,053 | 11/1967 | Stuttle | 128/78 |
| 3,362,402 | 1/1968 | Loeffel et al. | 128/78 |
| 3,717,143 | 2/1973 | Johnson | 128/78 |
| 3,812,862 | 5/1974 | Bernstein | 128/78 X |
| 3,920,008 | 11/1975 | Lehman | 128/96 |
| 3,926,183 | 12/1975 | Spiro | 128/78 |
| 4,022,197 | 5/1977 | Castiglia | 128/78 |

Primary Examiner—Robert E. Bagwill
Attorney, Agent, or Firm—Beaman & Beaman

[57] ABSTRACT

The invention constitutes an orthopedic garment of the torso encircling type for providing lumbosacral support, and the central region of the inner surface of the garment includes a removable orthosis brace whereby the garment may be selectively utilized for lumbosacral or lumbosacral-orthosis purposes. The removable brace is received within a cover including attachment means for releasably mounting the cover and brace to the garment inner surface, and the attachment means defined on the cover and band are vertically disposed along lateral edges of the orthosis cover.

9 Claims, 5 Drawing Figures

LUMBOSACRAL-ORTHOSIS ORTHOPEDIC SUPPORT

BACKGROUND OF THE INVENTION

The invention pertains to orthopedic lumbosacral garments having a removable orthosis.

To provide lumbosacral support it is well known to utilize torso encompassing garments of the band type which encircle the lower torso to restrict back movement, and such garments often include stays for reinforcing the garment, and buckles and clasps are usually employed in conjunction with straps to pull the garment snug about the torso.

The more serious back problems often require the orthopedic support provided by orthosis appliances, and such appliances usually consist of rigid or semi-rigid metallic members covered by cushioned material employed in conjunction with straps and fastening means for restricting back movement and providing rigid support to the back. Such orthoses devices are made in various configurations, and are commonly known as Taylor braces, Knight braces, or may take the form of hyperextension orthoses appliances or lumbosacral flexion orthoses braces.

A patient initially requiring the more rigid orthosis support may progress to a point where a lesser degree of support is desirable, such as lumbosacral type support, and in the past, it was necessary for the patient to purchase both an orthosis brace and a lumbosacral garment as the patient's condition improved. Othropedic garments are known wherein elements are mounted in the garment for increasing the rigidity thereof, and such elements may be removed for washing or other purposes, and such a device is shown in the assignee's U.S. Pat. No. 3,282,264. Also, orthopedic garments are known wherein various portions of the garment may be removed to accomodate various types of orthopedic treatments, and such a garment is shown in U.S. Pat. No. 3,362,402.

However, to the applicant's knowledge, an orthopedic garment which may be used for both lumbosacral and lumbosacral-orthosis purposes has not been provided which is of an economical construction, easy to wash and keep in a hygenic condition, and does not require special skills to produce modifications.

SUMMARY OF THE INVENTION

It is an object of the invention to provide a relatively inexpensive orthopedic garment capable of treating both lumbosacral and orthosis medical problems wherein the garment includes a removable rigid brace for selective cooperation with a lumbosacral band.

A further object of the invention is to provide an orthopedic garment of the lumbosacral-orthosis type wherein a rigid orthosis frame may be firmly mounted within a flexible body encircling band, and removed therefrom, without requiring special skills, and permits ready cleaning of the garment.

An additional object of the invention is to provide an orthopedic garment utilizing a removable orhtosis frame of a relatively rigid construction which may be mounted within a cover, and the cover and frame include lateral edges having attachment means, such as Velcro hook and loop material, for attaching the frame and cover to the lumbosacral band.

In the practice of the invention a lumbosacral garment band is formed of fabric having ends upon which straps, buckles and clasps are mounted for drawing the garment tightly about the torso. The central region of the garment engages the wearer's back, and stays are vertically oriented within the garment for producing the desired support and pressure distribution. The inner surface of the garment, adjacent the central region thereof, includes vertically oriented Velcro attachment means whereby the cover for a rigid orthosis brace may be attached to the inner surface of the band. The cover houses a relatively rigid metallic frame, whereby the frame, when located within the cover, provides the desired orthosis.

The assembled components of the garment may be readily separated for cleaning and washing purposes, and the use of the orthosis brace and cover is optional, but as the orthosis function can be achieved without purchasing additional straps and clasps the dual function of the garment may be achieved in a relatively inexpensive appliance.

BRIEF DESCRIPTION OF THE DRAWINGS

The aforementioned objects and advantages of the invention will be appreciated from the following description and accompanying drawings wherein.

DESCRIPTION OF THE PREFERRED EMBODIMENT

Figure 1:
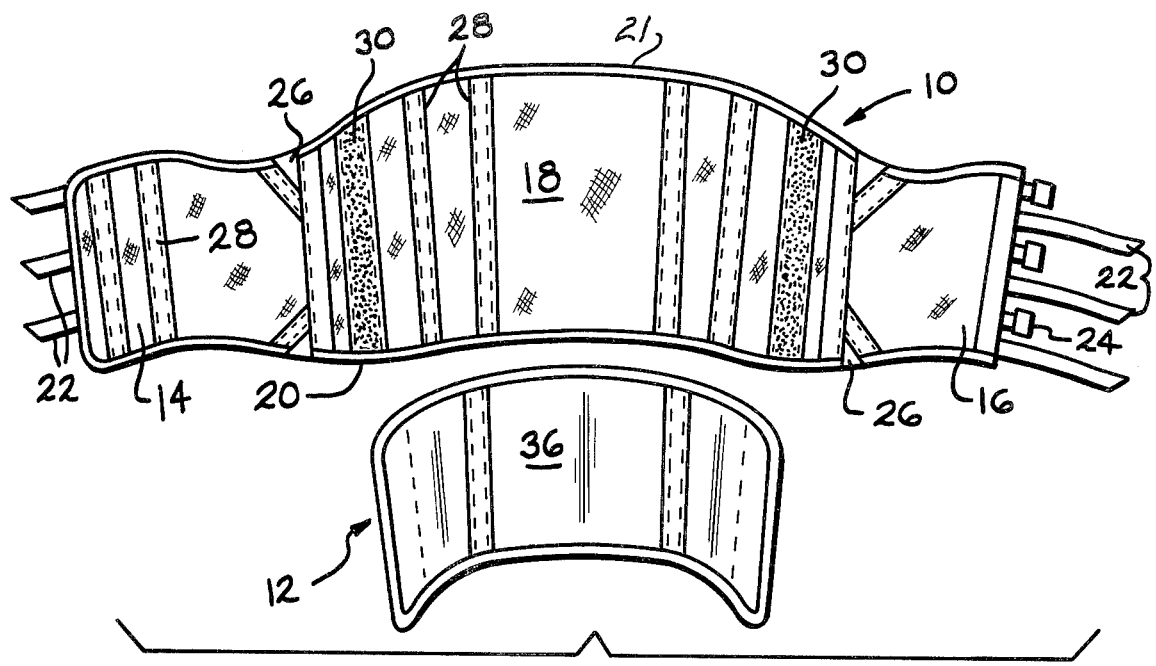
FIG. 1 is a perspective view of the inside of a garment in accord with the invention, the orthosis cover and frame being removed from the lumbosacral band and shown in "exploded" relationship.
Figure 2:
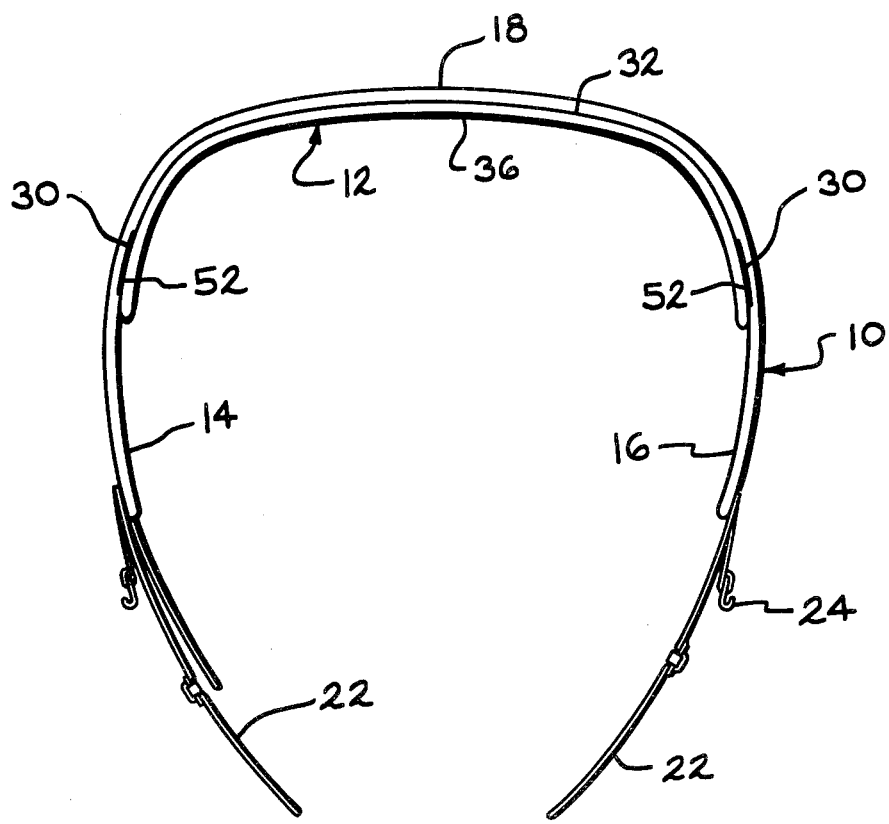
FIG. 2 is a top plan view of the band and orthosis assembled.

With reference to FIGS. 1 and 2, the garment basically consists of a lumbosacral band generally indicated at 10, and a substantially rigid orthosis brace assembly generally indicated at 12. The brace assembly 12 is adapted to be selectively attached to the inner surface of the lumbosacral band, and in this manner a single band may be used for both lumbosacral and lumbosacral-orthosis orthopedic purposes.

The band 10 is preferably formed of a fabric material having end regions 14 and 16 and a central region 18 of increased vertical dimension. The lower edge of the band is reinforced at 20, and the upper band edge 21 is likewise reinforced. The end regions of the band 10 are provided with straps 22 and buckles 24 whereby the band may be placed about the patient's torso and closed tightly by means of the cooperating straps and buckles, in the well known manner.

The band 10 is provided with elastic darts 26 to closely accomodate the garment to the patient's body, and a plurality of vertical pockets 28 are sewn in the garment for receiving semi-rigid stays as is conventional in garments of this type.

A pair of Velcro loop strips 30 are sewn to the inside surface 32 of the band 10 adjacent the intersection of the central 18 region with the end regions 14 and 16, and the Velcro strips 30 are vertically disposed extending between the upper and lower edges 20 and 21. The horizontal "width" of the central region 18 is sufficient to overlie the wearer's back, and the strips 30 will be disposed adjacent the sides of the wearer.

Figure 3:
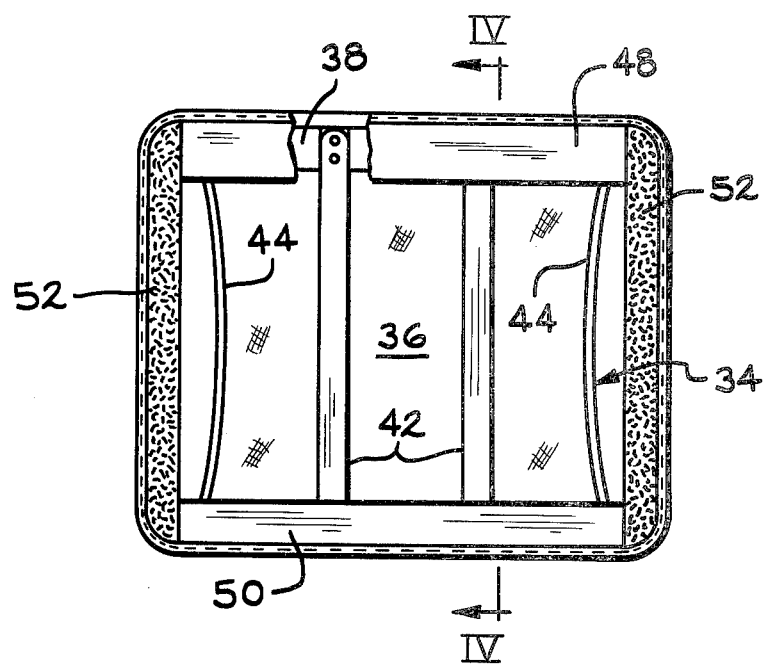
FIG. 3 is a rear, partially sectioned, view of the orthosis cover and frame.
Figure 4:
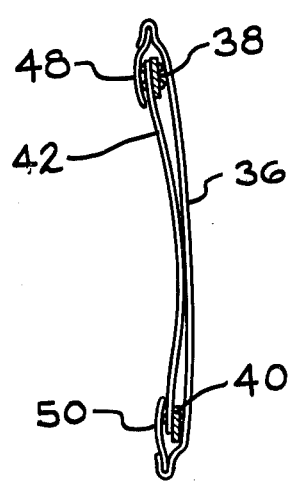
FIG. 4 is an elevational sectional view taken through the orthosis cover and frame along Section IV—IV of FIG. 3
Figure 5:
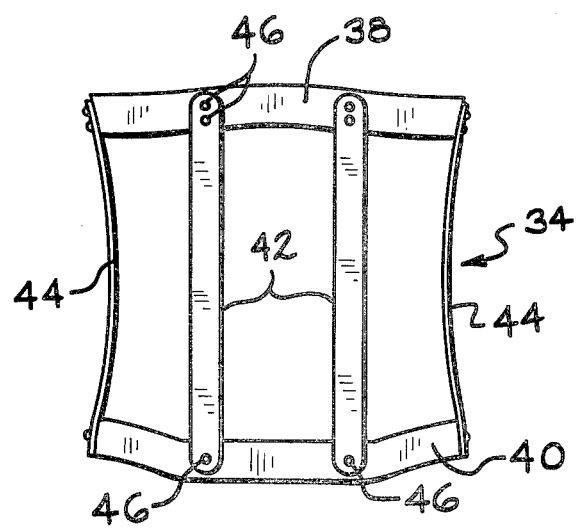
FIG. 5 is a rear view of the orthosis brace as removed from its cover.

The brace assembly 12 consists of a substantially rigid frame 34 located within a fabric cover 36. The frame, best illustrated in FIGS. 3-5, consists of arcuate upper and lower members 38 and 40 formed of aluminum and of a generally C-configuration as viewed from the top, as will be apparent from the configuration of the brace assembly as shown in FIG. 2. The members 38 and 40 are slightly contoured as will be appreciated from FIG. 5. The upper and lower frame members are interconnected by four vertical aluminum strips, i.e., a pair of back strips 42, and a pair of side strips 44, the side strips being slightly curved inwardly, FIG. 5, as are the back strips, as will be appreciated from FIG. 4. The vertical strips are attached to the upper and lower members by rivets 46 or equivalent fasteners wherein the six aluminum components constitute a relatively rigid, yet lightweight frame.

The frame 34 is partially covered by the cover 36 which is disposed over the inner surface of the frame whereby the frame itself is not visible from the inside of the garment, as will be appreciated from FIG. 1. The cover 36 is preferably formed of an attractive fabric, and adjacent its upper and lower edges vinyl strips 48 and 50 depend which extend downwardly and upwardly, respectively, sufficiently to overlap the frame upper and lower members 38 and 40 as will be appreciated from FIG. 4. At its lateral edges, the cover 36 includes Velcro strips 52 of the hook type, and the dimensional separation of the strips 52 as measured about the curvature of the frame 34, corresponds to the dimensional separation of the band Velcro strips 30. Thus, the brace assembly 12 may be quickly affixed to the inner surface 32 of the central region of the band by pressing the strips 52 against the strips 30 as will be appreciated from FIG. 2.

The dimensional vertical configuration of the brace assembly 12 is slightly less than the vertical dimension of the band central region 18 whereby approximately one inch of the band edge 21 extends above the upper edge of the cover, and approximately one inch of the band lower edge 20 extends below the lower-most portion of the brace assembly. Thus, in use, the presence or absence of the brace assembly within the band 10 is not apparent, and as the band will hold the brace assembly in close contact with the wearer's back the appliance may be readily worn underneath clothing, usually without detection.

The aforedescribed garment is used by patients requiring orthosis support greater than that provided by conventional lumbosacral garments, but less than that supplied by orthosis appliances of the Taylor and Knight types. Assuming the patient to require this type of orthosis support, the brace assembly 12 is mounted to the inside of the band by means of the Velcro strips 30 and 52, and the appliance is worn in the known manner whereby the tightening of the straps 22 will firmly hold the frame againse the wearer and produce the desired straightening and confinement. As the patient's condition improves, the orthosis provided by the brace assembly 13 may no longer be required, and the brace assembly may be removed from the band and the band used alone for lumbosacral support. Also, when its desired to wash the garment, when being used for a lumbosacral- orthosis support, the disassembly of the brace from the band, and the removal of the cover from the frame permits the garment to be readily cleaned.

It will be appreciated that the orthopedic garment described above provides a versatility not heretofore achieved with known orthopedic garments of either the lumbosacral or orthosis type, and it is appreciated that various modifications may be apparent to those skilled in the art without departing from the spirit and scope of the invention.

I claim:

1. A lumbosacral orthopedic device adapted to encircle the torso and having a removable orthosis appliance comprising, in combination, a flexible band member having inner and outer surfaces, a central region, end regions and upper and lower edges, mutually interconnectable connection means defined on said end regions, a substantially rigid frame disposed adjacent said inner surface at said central region, said frame including C-shaped substantially rigid and horizontal spaced members interconnected by substantially rigid elongated strips, and interengaging releasable fastening means defined on said frame and said band member releasably fastening said frame to said band member central region.

2. In a lumbosacral orthopedic device as in claim 1 wherein said frame is of a vertical dimension no greater than the vertical dimension separating said band member upper and lower edges at said central region.

3. In a lumbosacral orthopedic device as in claim 1, a flexible cover mounted upon said frame, said frame fastening means being defined on said cover.

4. In a lumbosacral orthopedic device as in claim 3, said cover including vertically extending lateral edges, said frame fastening means being defined on said lateral edges, and band member fastening means defined on said one surface extending between said upper and lower edges.

5. In a lumbosacral orthopedic device as in claim 4 wherein said cover and band member fastening means comprise interlocking Velcro strips.

6. In a lumbosacral orthopedic device as in claim 1 wherein said frame is disposed adjacent said band member inner surface and said releasable fastening means defined on said band member are located upon said band member inner surface.

7. A lumbosacral orthopedic device adapted to encircle the torso and having a removable orthosis appliance comprising, in combination, a flexible band member having inner and outer surfaces, a central region, end regions and upper and lower edges, mutually interconnectable connection means defined on said end regions, an elongated fastening strip affixed to said band member inner surface intermediate said central region and each end region extending between said upper and lower edges, a substantially rigid frame assembly removably secured to said band member central region adjacent said inner surface, said frame assembly including C-shaped substantially rigid and horizontal spaced members interconnected by substantially rigid elongated strips, a flexible cover having lateral edges mounted upon said frame assembly, and elongated fastening means defined on said lateral edges releasably interlocking with said fastening strips.

8. In a lumbosacral orthopedic device as in claim 7, said frame assembly being of a vertical dimension no greater than the vertical dimension of said band member at said central region.

9. In a lumbosacral orthopedic device as in claim 7 wherein said fastening strips and said fastening means comprise interlocking hook and loop components.

* * * * *